United States Patent
Malinowski

(10) Patent No.: US 10,525,474 B2
(45) Date of Patent: Jan. 7, 2020

(54) TEST TUBE CARRIER

(71) Applicant: Roche Diagnostics Operations, Inc., Indianapolis, IN (US)

(72) Inventor: Michal Malinowski, Bietigheim-Bissingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 176 days.

(21) Appl. No.: 15/801,568

(22) Filed: Nov. 2, 2017

(65) Prior Publication Data

US 2018/0056301 A1    Mar. 1, 2018

Related U.S. Application Data

(63) Continuation of application No. PCT/EP2016/059588, filed on Apr. 29, 2016.

(30) Foreign Application Priority Data

May 11, 2015 (EP) .................... 15167148

(51) Int. Cl.
*B01L 9/06* (2006.01)
*G01N 35/04* (2006.01)

(52) U.S. Cl.
CPC ............ *B01L 9/06* (2013.01); *G01N 35/04* (2013.01); *B01L 2200/023* (2013.01); *G01N 2035/0406* (2013.01)

(58) Field of Classification Search
None
See application file for complete search history.

(56) References Cited

U.S. PATENT DOCUMENTS

| 5,014,868 A | 5/1991 | Wittig et al. |
| 5,224,585 A | 7/1993 | Blanco et al. |
| 5,350,564 A | 9/1994 | Mazza et al. |
| 5,651,941 A | 7/1997 | Stark et al. |

(Continued)

FOREIGN PATENT DOCUMENTS

| EP | 0414644 A2 | 2/1991 |
| EP | 0916406 A2 | 5/1999 |

(Continued)

OTHER PUBLICATIONS

International Search Report dated Nov. 7, 2016, in Application No. PCT/EP2016/059588, 4 pages.

*Primary Examiner* — Paul S Hyun
(74) *Attorney, Agent, or Firm* — Roche Diagnostics Operations, Inc.

(57) ABSTRACT

A test tube carrier for transporting test tubes in a laboratory automation system is presented. The test tube carrier comprises a base body and at least three centering fingers attached to the base body. The centering fingers are distributed about a central axis (A). Each centering finger comprises an elongate, bent resilient element and a strut having a higher stiffness than the resilient element. The struts extend in parallel to the central axis (A). A first end of the associated resilient element is fixedly attached to the strut at an upper position and a second end of the resilient element contacts the strut at a lower position between the base body and the upper position. A laboratory distribution system having a number of test tube carriers, and a laboratory automation system comprising a laboratory distribution system are also presented.

8 Claims, 2 Drawing Sheets

(56) References Cited

U.S. PATENT DOCUMENTS

| | | | |
|---|---|---|---|
| 5,720,377 | A | 2/1998 | Lapeus et al. |
| 5,744,367 | A | 4/1998 | Talley et al. |
| 6,045,319 | A | 4/2000 | Uchida et al. |
| 6,074,612 | A | 6/2000 | Sagstetter |
| 6,274,092 | B1 | 8/2001 | Itoh |
| 6,343,690 | B1 | 2/2002 | Britton et al. |
| 6,571,934 | B1 | 6/2003 | Thompson et al. |
| 6,971,506 | B2 | 12/2005 | Hassinen et al. |
| 7,485,264 | B2 | 2/2009 | Itoh |
| 8,147,778 | B2 | 4/2012 | Pedrazzini |
| 2003/0143120 | A1 | 7/2003 | Ruediger et al. |
| 2005/0180896 | A1 | 8/2005 | Itoh |
| 2010/0155427 | A1 | 6/2010 | Lilienthal et al. |
| 2010/0186618 | A1 | 7/2010 | King et al. |
| 2010/0226828 | A1 | 9/2010 | Itoh |
| 2012/0118903 | A1 | 5/2012 | Norton et al. |
| 2012/0295358 | A1 | 11/2012 | Ariff et al. |
| 2013/0027185 | A1 | 1/2013 | Lavi |
| 2014/0234065 | A1 | 8/2014 | Heise et al. |
| 2014/0301916 | A1 | 10/2014 | Ohga et al. |
| 2015/0101911 | A1 | 4/2015 | Friedman |
| 2017/0131310 | A1 | 5/2017 | Volz et al. |
| 2017/0248623 | A1 | 8/2017 | Kaeppeli et al. |
| 2017/0248624 | A1 | 8/2017 | Kaeppeli et al. |

FOREIGN PATENT DOCUMENTS

| | | |
|---|---|---|
| EP | 2589966 A1 | 5/2013 |
| EP | 2799884 A1 | 11/2014 |
| EP | 2988134 A1 | 2/2016 |
| GB | 11486 A | 5/1911 |
| WO | 2011/138448 A1 | 11/2011 |
| WO | 2013/064656 A1 | 5/2013 |
| WO | 2014/138533 A1 | 9/2014 |

TEST TUBE CARRIER

CROSS-REFERENCE TO RELATED APPLICATIONS

This application is a continuation of PCT/EP2016/059588, filed Apr. 29, 2016, which is based on and claims priority to EP 15167148.4, filed May 11, 2015, which is hereby incorporated by reference.

BACKGROUND

The present disclosure relates to a test tube carrier for transporting test tubes in a laboratory automation system as well as to a laboratory distribution system having a number of test tube carriers and a laboratory automation system comprising a laboratory distribution system.

A laboratory automation system typically comprises a number of pre-analytical, analytical and/or post-analytical stations, in which samples, for example blood, saliva, swab and other specimens taken from the human body, are processed. It is generally known to provide test tubes containing the samples. The test tubes are also referred to as sample tubes.

Several test tubes can be placed in racks for a handling. In an alternative distribution system, test tubes are place in an upright or vertical position in so called test tube carriers or pucks having a retaining area for retaining test tubes.

Generally, in laboratory automation systems, different kinds of test tubes, in particular test tubes of different diameter are handled. It is further known to control the transport of the test tubes and/or a treatment of the sample contained in the test tube by a bar code provided on an outside surface of the test tube. For this purpose, the bar code should be readable during the transport and/or at all handling stations without needing to remove the test tube from the carrier.

Therefore, there is a need for a test tube carrier allowing for a secure support of different types of test tubes without hindering the readability of the bar code, or any other type of identification code, provided on an outside of the tube.

SUMMARY

According to the present disclosure, a test tube carrier for transporting test tubes in a laboratory automation system is presented. The test tube carrier can comprise a base body and at least three centering fingers attached to the base body. The centering fingers can be distributed about a central axis (A). Each centering finger can comprise an elongate, bent resilient element and a strut having a higher stiffness than the resilient element. The strut can extend in parallel to the central axis (A). A first end of the associated resilient element can be fixedly attached to the strut at an upper position. A second end of the resilient element can contact the strut at a lower position between the base body and the upper position when a test tube is inserted between the centering fingers and in the absence of a test tube. A contact portion of the resilient element between the first end and the second end can protrude towards the central axis (A).

Accordingly, it is a feature of the embodiments of the present disclosure to provide a test tube carrier allowing for a secure support of different types of test tubes without hindering a readability of the bar code or any other type of identification code provided on an outside of the tube. It is a further feature of the embodiments of the present disclosure to provide a laboratory distribution system and a laboratory automation system comprising a distribution system having a number of test tube carriers. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
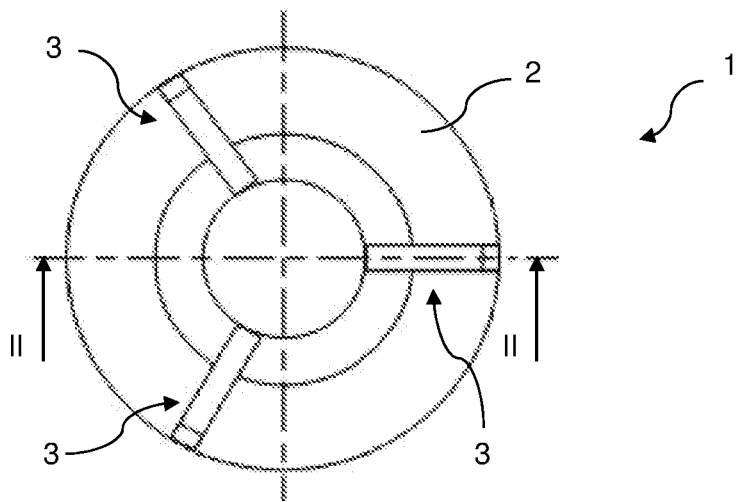
FIG. 1 illustrates a top view of a test tube carrier according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A test tube carrier for transporting test tubes in a laboratory automation system is presented. The test tube carrier can comprise a base body and at least three centering fingers attached to the base body. The centering fingers can be distributed about a central axis. Each centering finger can comprise an elongate, bent resilient element and a strut having a higher stiffness than the resilient element. The struts can extend substantially in parallel to the central axis. A first end of the associated resilient element can be fixedly attached to the strut at an upper position and a second end of the resilient element can contact the strut at a lower position between the base body and the upper position when a test tube is inserted between the centering fingers and in the absence of a test tube. A contact portion of the resilient element between the first end and the second end can protrude towards the central axis.

The base body can be part of a distribution system allowing the test tube carrier to be moved between different stations, for example by a conveyer belt, an assigned drive motor and/or a system, as described in WO 2013/064656 A1 and incorporated by reference, using a magnetically active device assigned to the carrier.

The resilient elements can be attached with a first end of the struts at an upper position. In one embodiment, the upper position can coincide to the upper end of the struts. In other embodiments, the struts can extend beyond the upper position. The second end of the resilient element can contact the associated strut at a position that can be lower than the upper position. The second end can contact the associated strut in the case the test tube carrier is empty as well as after receiving a test tube between the centering fingers.

When receiving a test tube between the centering fingers, the resilient elements can be deformed and the test tubes can be aligned with the central axis and clamped by the restoring forces. In use, different types of test tubes, in particular, test tubes of different diameters, can be transported by the test tube carrier. The resilient elements can allow for a compensation of different sizes. The struts having a higher stiffness than the resilient elements may not be deformed when receiving a test tube and prevent a permanent deformation of the centering fingers radially outwards. The resilient elements can be supported at the stiff struts at both ends allowing for a reliable guiding and alignment of the test tube when inserting the test tube as well as for a reliable restoration after removal of the test tube. A reliable restoration can be ensured even when holding test tubes with a larger diameter. Hence, a subsequent test tube with a smaller diameter can be retained without play.

The centering fingers can be evenly distributed about a circumference of a retaining area. The bar code, or other identification, provided at the outside of the tube can remain readable by humans or machines. The centering fingers, in particular, the resilient elements of the centering fingers of one test tube carrier in one embodiment can differ in design. In some embodiments, all centering fingers can be identical in design within tolerances and the centering fingers can be evenly distributed in order to ensure a reliable centering of the test tubes.

The resilient elements can comprise a contact portion between the first end and the second end. In some embodiments, the resilient elements can be adapted for a resilient deformation displacing the contact portion in parallel towards or away from an associated strut for receiving test tubes of different diameters. When displacing the contact portions in parallel towards or away from an associated strut, the effective contact portion in contact with received test tubes can be at least essentially the same for different test tubes of different diameters.

The resilient elements can be formed such that a contact portion of the resilient element between the first end and the second end can protrude towards the central axis. In some embodiments, the contact portion can be adapted for contacting a received test tube along an interrupted or uninterrupted contact line of a defined length extending in parallel to the central axis. In the context of the present disclosure, a contact line can be defined as a contact area comprising at least two distinct contact points. It can be understood by the person skilled in the art, that the terms "line" and "point" are not to be interpreted in a strict geometrical sense. Rather, a contact area of two bodies being in point contact can be in the form of a small ellipsoid. The contact portion, for example, can be a planar contact portion extending in parallel to the central axis and contacting a test tube having a circular cross section along a contact line. In other embodiments, a contact portion having a curved surface with a curvature of opposite sign than the received test tube can be provided. The defined length of the interrupted or uninterrupted contact line in particular embodiments can be at least between about 1% and about 100% of the length of the associated strut. In some embodiments, the defined length of the interrupted or uninterrupted contact line can be at least between about 40% and about 90% and in others, between about 60% and about 80%. In one embodiment, the contact portion can comprise two or more distinct contact areas, which can be offset to one another in the direction of the central axis. A received test tube can be in point contact or in line contact with each of the contact areas. In some embodiments, the contact portion can comprise one uninterrupted planar or curved contact area extending in parallel to the central axis.

The resilient elements can be adapted for a resilient deformation displacing the contact portion, in particular the contact portion contacting a test tube along a contact line, towards or away from an associated strut such that received test tubes of different sizes can be contacted at the contact portion, in particular along the interrupted or uninterrupted contact line of the defined length in parallel to the central axis. For a parallel displacement of the contact portion, in one embodiment, a first pivot leg can be arranged between the contact portion and the first end and a second pivot leg can be arranged between the contact portion and the second end. The contact portion can be coupled to the pivot legs via hinges such as, for example, via flexure hinges. When displacing the contact portion without altering the defined length of the interrupted or uninterrupted contact line, an overall contact region in which a received test tube contacts the resilient element can be independent of the diameter of the test tube. In the context of the application, a flexure hinge can be defined as a thinned out or otherwise processed part of material connecting two bodies, i.e. the contact portion and the pivot leg, made of the same material.

In one embodiment, the second end of at least one of the resilient elements can be in sliding contact with the associated strut at the lower position. Depending on the shape of the resilient element, when receiving a test tube, the second end of the resilient element can slide upwards or downwards along the strut.

In alternative or in addition, at least one of the resilient elements can be fixedly attached to the associated strut at the lower position. When attaching the resilient elements at both ends to the strut, guiding of the test tubes upon an insertion between the centering fingers can be enhanced.

The material of the elongate, bent resilient element can be chosen suitable for allowing repeatable deformation and sufficient restoration forces. In one embodiment, the resilient element can be in the form of a wire.

In some embodiments, the resilient elements can be in the form of resilient metal band. Suitable materials can be metals such as stainless steel, brass, bronze, spring steel or other similar resilient metals. The resilient metal band can be bent to contact with its two ends the strut and to protrude from the strut towards the central axis. A portion of the metal band can function as the contact portion. The portion in particular embodiments can extend in parallel to the central axis.

In some embodiments, at least one, preferably all of the resilient metal bands can be bent to form a substantially U-shaped member having a base extending in parallel to the central axis for contacting the received test tube. The U-shaped member can have two legs and the base arranged between the legs, so that the resilient element and the strut can form a trapezoid. In some embodiments, the resilient element and the strut can form a parallelogram. The base, the first leg and the second leg can function as the contact portion, the first pivot leg and the second pivot leg, respectively. Hinges between the contact portion and the first and the second leg in one embodiment can be formed by bending or folding the resilient metal band. In addition, in one embodiment, the metal band can be thinned out in the region of bends or folds for forming flexure hinges. When inserting the test tube, an angle between the legs and the base as well as between the legs and the strut can change and the height of the trapezoid or parallelogram perpendicular to the strut can be decreased. In the case both legs are fixedly attached to the strut, the legs can be swiveled in the same angular direction. In the case the second end is in sliding contact, embodiments can be conceivable, in which the legs can be swiveled in opposite directions upon receiving the test tube.

In some embodiments, the U-shaped member can comprise a first leg attached to the upper of the associated strut. The strut and the first leg can form an acute angle. In other words, the first leg can extend from the strut toward the central axis and toward the base body. When arranging the first leg at an acute angle, the first legs can form an insertion aid for the test tubes causing pre-alignment of the test tubes with the central axis.

As mentioned above, the legs, the base and the strut can form a trapezoid. In some embodiments, the U-shaped member can comprise a second leg extending in parallel to the first leg. In other words, the legs, the base and the strut can form a parallelogram. Both legs can be swiveled towards the strut upon the insertion of a test tube.

In one embodiment, the base of the U-shaped member can be bent to form a contact portion with at least two distinct contact areas. Thereby, a total area of a contact portion between the test tube and the base can be decreased.

In one embodiment, the test tubes can be placed on a flat base body and retained only by the centering fingers. In some embodiments, the base body can have a recess such as, for example, a chamfered recess adapted for accommodating a bottom of a test tube. The size or depth of the recess and an orientation of the walls of the recess can be chosen to allow for an accommodation of different types of test tubes without hindering a readability of the bar code, or any other type of identification code, provided on an outside of the test tube.

In one embodiment, the struts can be fixedly attached to the base body such as, for example, by soldered, welded, or clued to the base body. In some embodiments, at least one of the struts can be releasably attached to base body. Hence, the central fingers can be replaced if worn-out, without the necessity to replace the base body. In some embodiments, a plug-in connection can be provided. The struts can be inserted into receiving openings extending in the axial direction of the struts. The ends of the struts can be inserted into the receiving openings and the receiving openings in one embodiment do not have rotation symmetry to ensure an insertion of the struts with a suitable orientation.

A laboratory distribution system can be provided having a number of test tube carriers. The laboratory distribution system in one embodiment can comprise a transport device with a transport plane adapted to carry the number of test tube carriers. The carriers can each comprise at least one magnetically active device. The transport device can comprise a number of electromagnetic actuators. The electromagnetic actuators can be stationary arranged below the transport plane and can be adapted to move a test tube carrier placed on top of the transport plane by applying a magnetic force to the test tube carrier. However, the present disclosure may not be limited to such a laboratory distribution system. In other embodiments, for example a conveyer belt or guiding rails can be provided for moving the test tube carriers. In still another embodiment, each test tube carrier can be provided with a drive motor.

A laboratory automation system with a number of pre-analytical, analytical and/or post-analytical stations and with a distribution system having a number of test tube carriers can also be provided.

Figure 2:
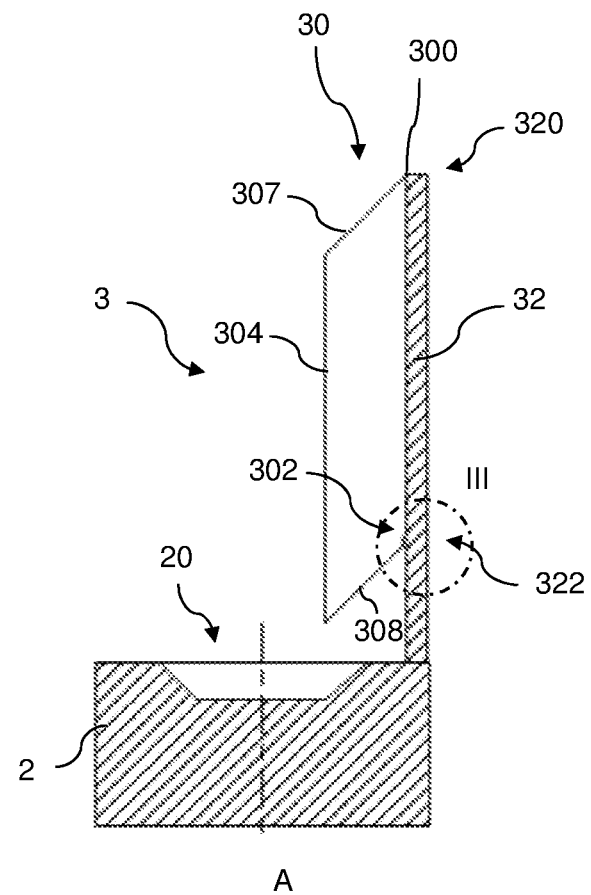
FIG. 2 illustrates a sectional view of the test tube carrier of FIG. 1 along a line II-II according to an embodiment of the present disclosure.

FIGS. 1 and 2 show a top view and a sectional view of a first embodiment of a test tube carrier 1 for transporting test tubes (not shown in FIGS. 1 and 2) in a laboratory distribution system of a laboratory automation system.

The test tube carrier 1 can comprise a base body 2 and three centering fingers 3 attached to the base body 2. The three centering fingers 3 can be evenly distributed about a central axis A. In other embodiments, more than three centering fingers 3 can be provided, for example, four or five centering fingers 3. In the embodiment shown, the base body 2 can have a circular cylindrical shape, which can be concentric to the central axis A. However, this shape is to be understood only as an example, other shapes are conceivable. The base body can be adapted to the requirements of a laboratory distribution system.

The base body 2 can have a chamfered recess 20, which can be concentric to the central axis A and adapted for accommodating a bottom of a test tube.

The centering fingers 3 can each comprise an elongate, bent resilient element 30 and a strut 32. Due to material differences and/or due to a shape, the strut 32 can have a higher stiffness than the resilient elements 30.

The three struts 32 can each extend in parallel to the central axis A. A connection of the struts 32 to the base body 2 is depicted only diagrammatically. A suitable connection can be chosen by the person skilled in the art. In one embodiment, the struts 32 can be releasably attached to the base body 2 allowing a replacement of the struts 32 in case the centering fingers 3 are worn-out.

In the embodiment shown, the resilient elements 30 can be in the form of bent resilient metal bands such as, for example, bent spring steel bands. A first end 300 of the resilient metal band can be fixedly attached to the strut 32 at an upper position 320, which the upper position 320 can coincide with the upper end of the strut 32. A second end 302 of the resilient metal band can contact the strut 32 at a lower position 322, which the lower position 322 can be situated between the base body 2 and the upper position 320.

The struts 32 can be arranged outside of a retaining area for the test tubes and the resilient elements 30. In one embodiment, a contact portion of the resilient elements 30 provided between the first end 300 and the second end 302 can protrude from the struts 32 towards the central axis A and into the retaining area for the test tubes.

In the embodiment shown, the resilient metal bands provided as the resilient elements 30 can be bent to form a substantially U-shaped member having base 304, a first leg 307 and a second leg 308, each.

The base 304 of each of the U-shaped members can function as the contact portion. It can extend in parallel to the central axis A for contacting the received test tube (not shown) along a contact line. The first legs 307 of each of the U-shaped members can be attached to the strut 32 at the upper position 320. The strut 32 and the first leg 307 can form an acute angle. Thereby, the first legs 307 can function as an insertion aid for a pre-alignment of the test tubes.

In the embodiment shown, the second leg 308 can extend substantially in parallel to the first leg 307. A free end of the second leg 308 can contact the strut 32 at the lower position 322.

When inserting a test tube between the centering fingers 3, the resilient elements can be resiliently deformed for receiving test tubes of different diameters. The first leg 300 and the second leg 302 can be pivoted towards the associated strut 32 for displacing the base 304 in parallel towards the associated strut 32. Thus, the base 304 functioning as a contact portion contacts can receive test tubes of different diameters along a contact line. The length $L_{CL}$ of the contact line can be the same for test tubes of different diameter. In the embodiment shown in FIG. 2, the length $L_{CL}$ of the uninterrupted contact line can be between about 70% and 80% of the length $L_S$ of the associated strut 32. After removal of the test tube, the restoration force of the resilient element 30 can cause the first leg 300 and the second leg 302 to be pivoted away from the associated strut 32 for displacing the base 304 in parallel away from the associated strut 32.

Figure 3:
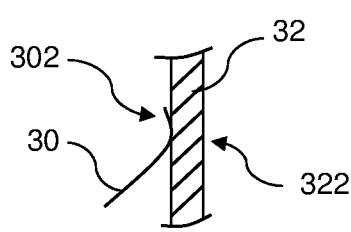
FIG. 3 illustrates a detail view of section III of FIG. 2 according to an embodiment of the present disclosure.

FIG. 3 shows detail of the section III of FIG. 2. As can be seen in FIG. 3, in the embodiment shown in FIGS. 1 to 3, the second ends 302 of the resilient elements 30, more particular of the second legs 308, can be in sliding contact with the associated strut 32 at the lower position 322.

Figure 4:
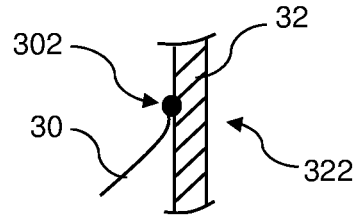
FIG. 4 illustrates a detail of a test tube carrier similar to FIG. 3 according to a second embodiment of the present disclosure.

FIG. 4 shows a detail of a second embodiment of a test tube carrier similar to FIG. 3. The test tube carrier according to the second embodiment in large parts can correspond to test tube carrier shown in FIGS. 1 to 3. In contrast to the embodiment shown in FIG. 3, the second end 302 of the resilient element 30 shown, preferably of all resilient elements, can be fixedly attached to the associated strut 32 at the lower position 322.

Figure 5:
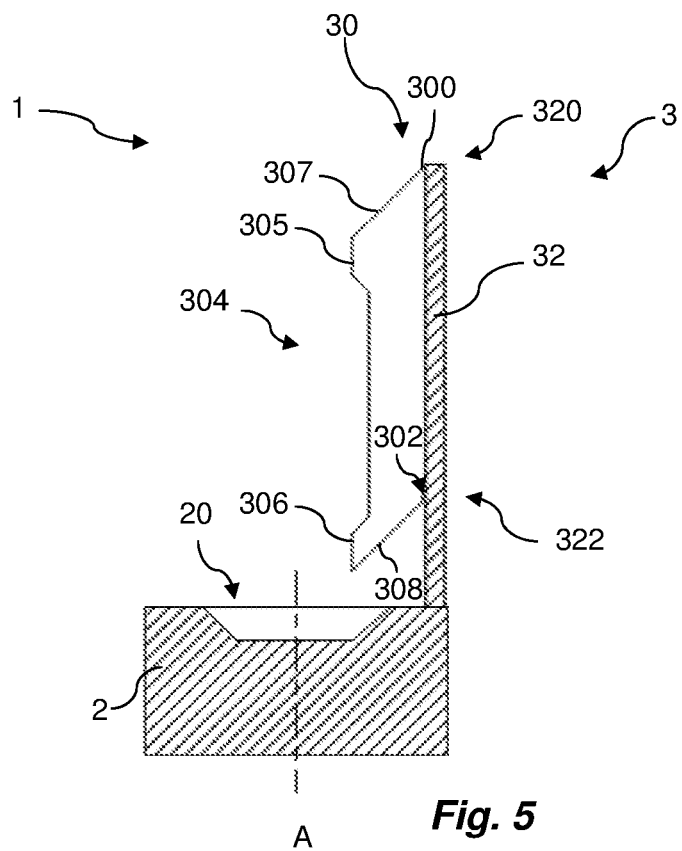
FIG. 5 illustrates a sectional view of a test tube carrier similar to FIG. 2 according to a third embodiment of the present disclosure.

FIG. 5 shows a sectional view of a third embodiment of a test tube carrier 1 similar to FIG. 2. The test tube carrier 1 according to the second embodiment in large parts can correspond to test tube carrier 1 shown in FIG. 1 to 3 or 4 and for a detailed description, reference is made to the above description. In contrast to the embodiments described above, the base 304 of the U-shaped member can be bent to form a contact portion with at least two distinct contact areas 305, 306, contacting the received test tube at two distinct areas. A test tube inserted between the centering fingers 3 shown in FIG. 5 can contact the contact portion along an interrupted contact line, which can extend across both contact areas 305, 306. In the embodiment shown in FIG. 5, the length $L_{305}$, $L_{306}$ of each the two distinct contact areas can be between about 5% and 10% of the length $L_S$ of the associated strut 32. The overall length $L_{CL}$ of the interrupted contact line can be between about 70% and 80% of the length $L_S$ of the associated strut 32.

Figure 6:
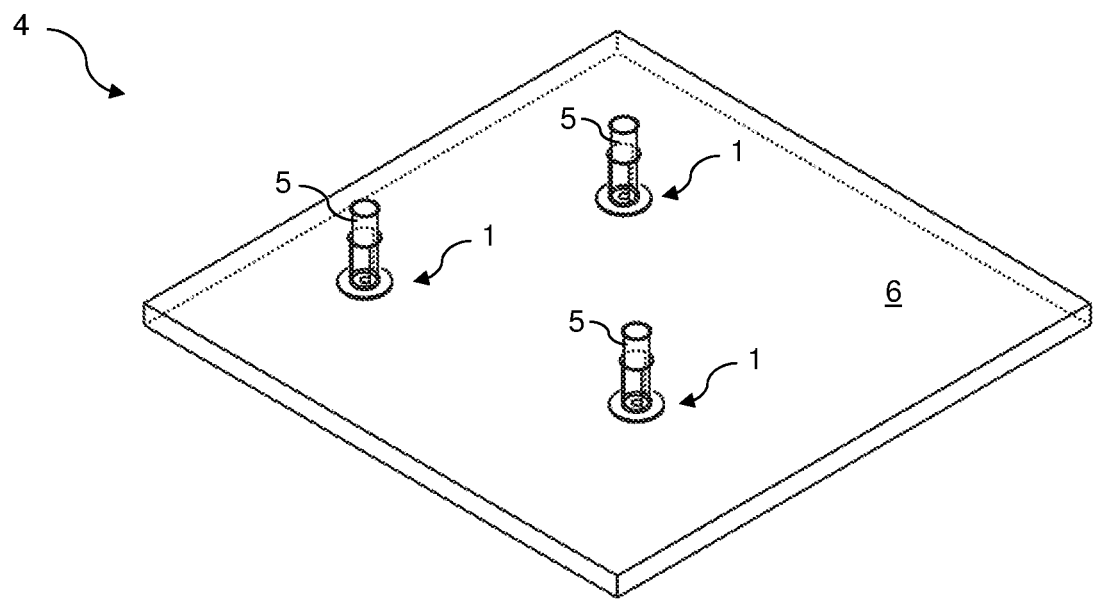
FIG. 6 illustrates a perspective view of a laboratory distribution system comprising a number of test tube carriers according to an embodiment of the present disclosure.

FIG. 6 shows a perspective view of a laboratory distribution system 4 comprising a number of test tube carriers 1 and a transport device with a transport plane 6 adapted to carry the number of test tube carriers 1. Test tubes 5 can be received by the test tube carriers 1 and moved over the transport plane 6 to a desired destination.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A test tube carrier for transporting test tubes in a laboratory automation system, the test tube carrier comprising:
a base body; and
at least three centering fingers attached to the base body, wherein the centering fingers are distributed about a central axis (A), wherein each centering finger comprises an elongate, bent resilient element and a strut having a higher stiffness than the resilient element, wherein the strut extends in a parallel manner to the central axis (A), wherein a first end of the associated resilient element is fixedly attached to the strut at an upper position, wherein a second end of the resilient element contacts the strut at a lower position between the base body and the upper position when a test tube is inserted between the centering fingers and in the absence of a test tube, wherein a contact portion of the resilient element between the first end and the second end protrudes towards the central axis (A), wherein the resilient elements are in the form of resilient metal bands, wherein at least one of the resilient metal bands is bent to form a U-shaped member having a base having at least a section extending parallel to the central axis to define the contact portion for contacting the received test tube, wherein the U-shaped member comprises:
a first leg attached to the upper position of the associated strut, wherein the strut and the first leg form an acute angle, and
a second leg extending parallel to the first leg.

2. The test tube carrier according to claim 1, wherein each resilient elements is adapted for a resilient deformation displacing the contact portion in a parallel manner towards or away from an associated strut for receiving test tubes of different diameters.

3. The test tube carrier according to claim 1, wherein the contact portion is adapted for contacting a received test tube along an interrupted or uninterrupted contact line of a defined length extending in-parallel to the central axis (A).

4. The test tube carrier according to claim 1, wherein the second end of at least one of the resilient elements is in sliding contact with the associated strut at the lower position.

5. The test tube carrier according to claim 1, wherein the second end of at least one of the resilient elements is fixedly attached to the associated strut at the lower position.

6. The test tube carrier according to claim 1, wherein the base of the U-shaped member is bent to form the contact portion with at least two distinct contact areas extending in parallel to the central axis.

7. The test tube carrier according to claim 1, wherein the base body has a recess adapted for accommodating a bottom of a test tube.

8. The test tube carrier according to claim 1, wherein at least one of the struts is releasably attached to the base body.

* * * * *